(12) United States Patent
Nukui

(10) Patent No.: US 7,334,940 B2
(45) Date of Patent: Feb. 26, 2008

(54) SCATTER MEASUREMENT METHOD, SCATTER CORRECTION METHOD, AND X-RAY CT APPARATUS

(75) Inventor: Masatake Nukui, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 382 days.

(21) Appl. No.: 11/030,511

(22) Filed: Jan. 6, 2005

(65) Prior Publication Data

US 2005/0147200 A1    Jul. 7, 2005

(30) Foreign Application Priority Data

Jan. 7, 2004    (JP) .............................. 2004-001941

(51) Int. Cl.
*G01D 18/00* (2006.01)

(52) U.S. Cl. .............................. 378/207; 378/7; 378/86

(58) Field of Classification Search .................... 378/7, 378/86, 154, 207, 205
See application file for complete search history.

(56) References Cited

U.S. PATENT DOCUMENTS

| | | | |
|---|---|---|---|
| 4,114,041 A | | 9/1978 | Oliver |
| 5,615,279 A | | 3/1997 | Yoshioka et al. |
| 5,666,391 A | * | 9/1997 | Ohnesorge et al. ............ 378/7 |
| 5,905,809 A | | 5/1999 | Timmer |
| 6,173,033 B1 | * | 1/2001 | Klingenbeck-Regn et al. ............................. 378/20 |
| 6,175,609 B1 | | 1/2001 | Edic et al. |
| 6,256,367 B1 | | 7/2001 | Vartanian |
| 6,408,049 B1 | | 6/2002 | Edic et al. |
| 6,687,326 B1 | | 2/2004 | Bechwati et al. |
| 2003/0198314 A1 | | 10/2003 | Saito |

FOREIGN PATENT DOCUMENTS

| | | |
|---|---|---|
| JP | 07-213517 | 8/1995 |
| JP | 08-131431 | 5/1996 |
| JP | 11-299768 | 11/1999 |

OTHER PUBLICATIONS

Venselaar et al., Is there a need for a revision table of equivalent square fields for the determination of phantom scatter correction factors?, 1997, Phys. Med. Biol., vol. 42, pp. 2369-2381.*

European Search Report; Munich; Mar. 31, 2005; EP04258059; 2 pgs.

* cited by examiner

*Primary Examiner*—Edward J. Glick
*Assistant Examiner*—John M Corbett
(74) *Attorney, Agent, or Firm*—Armstrong Teasdale LLP

(57) ABSTRACT

A method for correcting scatter in multi-slice imaging wherein, a projection p and a scatter correction factor $R(d, do)$ are stored in association with each other, a projection p is determined from data $D0$ collected by imaging a subject with an X-ray beam with a beam thickness d using a detector with a detector thickness do, the scatter correction factor $R(d, do)$ associated with the projection p is determined, and the data $D0$ is multiplied by the scatter correction factor $R(d, do)$ to obtain scatter-corrected data $D1$.

20 Claims, 6 Drawing Sheets

FIG. 3A
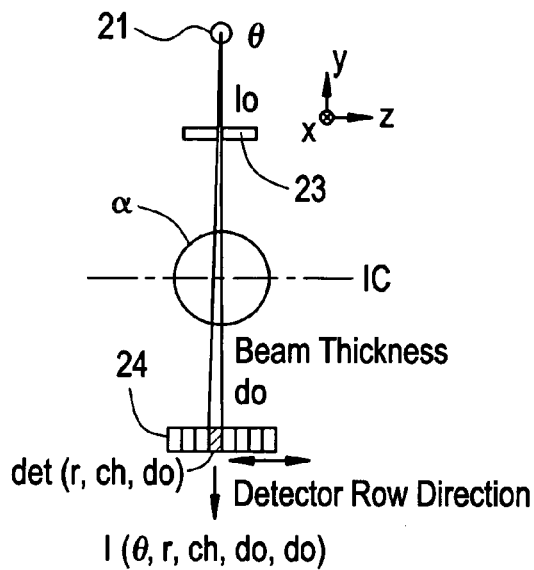
I (θ, r, ch, do, do)
FIG. 3B
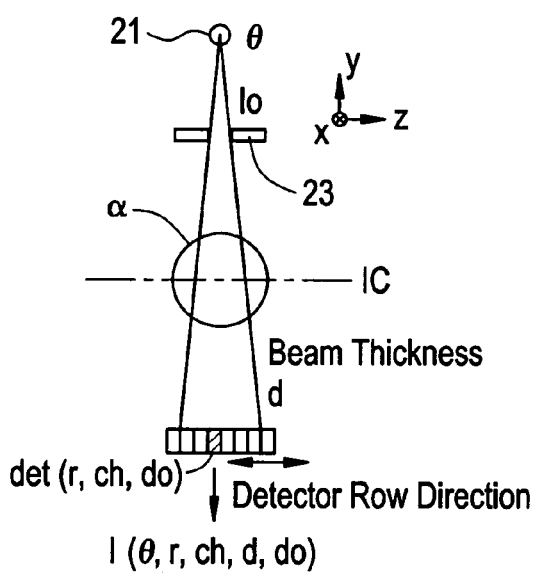
I (θ, r, ch, d, do)
FIG. 4
Scatter Correction Factor
R(θ, r, ch, d, do)
Beam Thickness
- d=d4
- d=d3
- d=d2
- d=d1
Projection p or sum Ar, Ac or V

SCATTER MEASUREMENT METHOD, SCATTER CORRECTION METHOD, AND X-RAY CT APPARATUS

CROSS REFERENCE TO RELATED APPLICATIONS

This application claims the benefit of Japanese Application No. 2004-001941 filed Jan. 7, 2004.

BACKGROUND OF THE INVENTION

The present invention relates to a scatter measurement method, a scatter correction method, and an X-ray CT (computer tomography) apparatus, and more particularly to a scatter measurement method for measuring scatter in multi-slice imaging, a scatter correction method for correcting scatter in multi-slice imaging, and an X-ray CT apparatus.

There are known several kinds of conventional scatter correction methods for use in an X-ray CT apparatus employing a single-row detector (for example, see Patent Documents 1 and 2). Moreover, a scatter correction method applicable to an X-ray CT apparatus employing a multi-row detector has been proposed (for example, see Patent Document 3).

[Patent Document 1] Japanese Patent Application Laid Open No. H7-213517.
[Patent Document 2] Japanese Patent Application Laid Open No. H8-131431.
[Patent Document 3] Japanese Patent Application Laid Open No. H11-299768.

In performing multi-slice imaging using a multi-row detector having a plurality of detector rows, the imaging is more affected by scatter because the beam thickness is larger than the thickness of the individual detectors (or detector row thickness).

The conventional scatter correction method for use in an X-ray CT apparatus employing a single-row detector, however, does not take such a condition into account, and there is a problem of the method not being applicable to such a condition.

The conventional scatter correction method for use in an X-ray CT apparatus employing a multi-row detector can be applied to such a condition, but it requires image reconstruction to be conducted twice, leading to a problem of a high computational load.

BRIEF DESCRIPTION OF THE INVENTION

It is therefore an object of the present invention to provide a scatter measurement method for measuring scatter in multi-slice imaging, a scatter correction method for correcting scatter in multi-slice imaging, and an X-ray CT apparatus.

It its first aspect, the present invention provides a scatter measurement method characterized in comprising: measuring data I(do, do) by imaging an object to be imaged with a beam thickness equal to a detector thickness do; measuring data I(d, do) by imaging the object to be imaged with a beam thickness d larger than the detector thickness do; and determining an amount of scatter S(d, do) based on a difference between said data I(do, do) and said data I(d, do).

The designation (,) in the references to the data I(do, do) data I(d, do) and amount of scatter S(d, do) represents (beam thickness, detector thickness).

According to the scatter measurement method of the first aspect, since the detector thickness do is invariant while the beam thickness is variant, the increment from the data I(do, do) to the data I(d, do) may be considered to be exclusively caused by scatter. Therefore, the amount of scatter S(d, do) can be determined based on the difference between the data I(do, do) and data I(d, do).

Scatter involved in the data I(do, do) is ignored. Alternatively, a conventionally known scatter correction method may be applied to further correct scatter involved in the data I(do, do) because the data I(do, do) may be regarded as data of a single-row detector.

In its second aspect, the present invention provides a scatter measurement method characterized in comprising: measuring data I(do, do) by imaging an object to be imaged with a beam thickness equal to a detector thickness do; measuring data I(d, do) by imaging the object to be imaged with a beam thickness d larger than the detector thickness do; and determining a scatter correction factor R(d, do) based on a ratio between said data I(do, do) and said data I(d, do).

According to the scatter measurement method of the second aspect, since the detector thickness do is invariant while the beam thickness is variant, the increment from the data I(do, do) to the data I(d, do) may be considered to be exclusively caused by scattering. Therefore, based on the ratio between the data I(do, do) and data I(d, do), there can be determined a ratio R(d, do) between a "signal component" and a "(signal component)+(scatter component)" in data D(d, do) obtained by imaging a subject with the beam thickness d larger than the detector thickness do. The ratio R(d, do) is called scatter correction factor because the "scatter component" can be removed by multiplying the data D(d, do) by the ratio R(d, do).

In its third aspect, the present invention provides the scatter measurement method having the aforementioned configuration, characterized in comprising: storing a projection p of the object to be imaged and the scatter correction factor or smoothed scatter correction factor R(d, do) in association with each other.

Representing the intensity of X-rays passing through an object to be imaged and intercepted by a detector det(r, ch) at a channel ch in a detector row r as I(r, ch), and the intensity of X-rays before passing through the object to be imaged as Io(r, ch), the projection p of the object to be imaged is given by:

$$p(r, ch) = -\log\{I(r, ch)\} + \log\{Io(r, ch)\} = -\log\{I(r, ch)/Io(r, ch)\}.$$

The projection p represents a property of the object to be imaged, and it may be considered to correlate with the amount of scatter. In other words, the projection p and scatter correction factor R(d, do) may be considered to correlate with each other.

According to the scatter measurement method of the third aspect, the projection p and the scatter correction factor or smoothed scatter correction factor R(d, do) are stored in association with each other. This allows the scatter correction factor R(d, do) to be appropriately used in association with the property of a subject.

Representing the intensity of X-rays passing through a subject and intercepted by a detector det(r, ch) at a channel ch in a detector row r as D(r, ch), and the intensity of X-rays before passing through the subject as Do(r, ch), the projection p of the subject is given by:

$$p(r, ch) = -\log\{D(r, ch)\} + \log\{Do(r, ch)\} = -\log\{D(r, ch)/Do(r, ch)\}.$$

Moreover, since the scatter correction factor R(d, do) is different from a detector det(r, ch) to a detector det(r, ch), if the scatter correction factor R(d, do) is directly used for scatter correction, the difference in scatter-corrected data D1 between adjacent channels is magnified beyond the difference in original data D0, possibly resulting in formation of a step-like difference.

By storing the smoothed scatter correction factor R(d, do), the step-like difference between adjacent channels can be avoided.

In its fourth aspect, the present invention provides the scatter measurement method having the aforementioned configuration, characterized in comprising: collecting data using a multi-row detector; and storing a sum Ar of the projection p of the object to be imaged in a detector row direction or a sum Ac thereof in a channel direction, and the scatter correction factor or smoothed scatter correction factor R(d, do) in association with each other.

The sum Ar of the projection p of an object to be imagined in the detector row direction is a value obtained by adding the projection p(r, ch) of the object to be imaged at the same channel across all detector rows or across a plurality of detector rows including a detector row r. That is, the sum Ar is given by:

$$Ar(r, ch) = \sum_{k=1}^{r} P(k, ch)$$

or $$Ar(r, ch) = \sum_{r} P(r, ch)$$

The sum Ac of the projection p of an object to be imaged in the channel direction is a value obtained by adding the projection p(r, ch) of the object to be imaged in the same detector row across all channels or across a plurality of channels including a channel ch. That is, the sum Ac is given by:

$$Ac(r, ch) = \sum_{k=1}^{ch} P(r, k)$$

or $$Ac(r, ch) = \sum_{ch} P(r, ch)$$

The sum Ar or Ac of the projection p represents a property of the object to be imaged, and it may be considered to correlate with the amount of scatter. In other words, the sum Ar or Ac and scatter correction factor R(d, do) may be considered to correlate with each other.

According to the scatter measurement method of the fourth aspect, the sum Ar or Ac and the scatter correction factor or smoothed scatter correction factor R(d, do) are stored in association with each other. This allows the scatter correction factor R(d, do) to be appropriately used in association with the property of a subject.

The sum Ar of a projection p of a subject in the detector row direction is a value obtained by adding the projection p(r, ch) of the subject at the same channel across all detector rows or across a plurality of detector rows including a detector row r. That is, the sum Ar is given by:

$$Ar(r, ch) = \sum_{k=1}^{r} p(k, ch)$$

or $$Ar(r, ch) = \sum_{r} p(r, ch)$$

The sum Ac of a projection p of a subject in the channel direction is a value obtained by adding the projection p(r, ch) of the subject in the same detector row across all channels or across a plurality of channels including a channel ch. That is, the sum Ac is given by:

$$Ac(r, ch) = \sum_{k=1}^{ch} p(r, k)$$

or $$Ac(r, ch) = \sum_{ch} p(r, ch)$$

In its fifth aspect, the present invention provides the scatter measurement method having the aforementioned configuration, characterized in comprising: collecting data using a multi-row detector; and storing a sum V of the projection p of the object to be imaged in a detector row direction and channel direction, and the scatter correction factor or smoothed scatter correction factor R(d, do) in association with each other.

The sum V of the projection p of an object to be imaged in the detector row direction and channel direction is a value obtained by adding the projection p(r, ch) of the object to be imaged across all detector rows and all channels or across a plurality of detector rows and a plurality of channels including a detector det(r, ch). That is, the sum V is given by:

$$V(r, ch) = \sum_{ch} \sum_{r} p(r, ch)$$

The sum V of the projection p represents a property of the object to be imaged, and it may be considered to correlate with the amount of scatter. In other words, the sum V and scatter correction factor R(d, do) may be considered to correlate with each other.

According to the scatter measurement method of the fifth aspect, the sum V and scatter correction factor or smoothed scatter correction factor R(d, do) are stored in association with each other. This allows the scatter correction factor R(d, do) to be appropriately used in association with the property of a subject.

The sum V of a projection p of a subject in the detector row direction and channel direction is a value obtained by adding the projection p(r, ch) of the subject across all detector rows and all channels or across a plurality of detector rows and a plurality of channels including a detector det(r, ch). That is, the sum V is given by:

$$V(r, ch) = \sum_{ch} \sum_{r} p(r, ch)$$

In its sixth aspect, the present invention provides a scatter correction method characterized in comprising: after storing the projection p and scatter correction factor or smoothed scatter correction factor R(d, do) in association with each other as in the aforementioned configuration, determining a projection p from data D0 collected by imaging a subject by an X-ray beam with a beam thickness d using a detector with a detector thickness do; determining the scatter correction factor R(d, do) associated with that projection p; and obtaining scatter-corrected data D1 by multiplying the data D0 by the scatter correction factor R(d, do).

The projection p represents a property of a subject, and it may be considered to correlate with the amount of scatter. In other words, the projection p and scatter correction factor R(d, do) may be considered to correlate with each other.

According to the scatter correction method of the sixth aspect, the projection p and scatter correction factor or smoothed scatter correction factor R(d, do) are stored in association with each other, and then the scatter correction factor R(d, do) associated with the projection p of the subject can be read and used to perform scatter correction while appropriately using the scatter correction factor R(d, do) in association with the property of the subject.

In its seventh aspect, the present invention provides a scatter correction method characterized in comprising: after storing the sum Ar or Ac and scatter correction factor or smoothed scatter correction factor R(d, do) in association with each other as in the aforementioned configuration, determining a projection p from data collected by imaging a subject by an X-ray beam with a beam thickness d using a multi-row detector including a detector with a detector thickness do; determining a sum Ar of the projection p in the detector row direction or a sum Ac thereof in the channel direction; determining the scatter correction factor R(d, do) associated with the sum Ar or Ac; and obtaining scatter-corrected data D1 by multiplying the data D0 collected using the detector with the detector thickness do by the scatter correction factor R(d, do).

The sum Ar or Ac of the projection p represents a property of a subject, and it may be considered to correlate with the amount of scatter. In other words, the sum Ar or Ac and scatter correction factor R(d, do) may be considered to correlate with each other.

According to the scatter correction method of the seventh aspect, the sum Ar or Ac and scatter correction factor or smoothed correction factor R(d, do) are stored in association with each other, and then the scatter correction factor R(d, do) associated with the sum Ar or Ac of the projection p of the subject can be read and used to perform scatter correction while appropriately using the scatter correction factor R(d, do) in association with the property of the subject.

In its eight aspect, the present invention provides a scatter correction method characterized in comprising: after storing the sum V and scatter correction factor or smoothed scatter correction factor R(d, do) in association with each other as in the aforementioned configuration, determining a projection p from data collected by imaging a subject by an X-ray beam with a beam thickness d using a multi-row detector including a detector with a detector thickness do; determining a sum V of the projection p in the detector row direction and channel direction; determining the scatter correction factor R(d, do) associated with the sum V; and obtaining scatter-corrected data D1 by multiplying the data D0 collected using the detector with the detector thickness do by the scatter correction factor R(d, do).

The sum V of the projection p represents a property of a subject, and it may be considered to correlate with the amount of scatter. In other words, the sum V and scatter correction factor R(d, do) may be considered to correlate with each other.

According to the scatter correction method of the eighth aspect, the sum V and scatter correction factor or smoothed scatter correction factor R(d, do) are stored in association with each other, and then the scatter correction factor R(d, do) associated with the sum V of the projection p of the subject can be read and used to perform scatter correction while appropriately using the scatter correction factor R(d, do) in association with the property of the subject.

In its ninth aspect, the present invention provides the scatter correction method having the aforementioned configuration, characterized in comprising: obtaining scatter-corrected and smoothed data D2 by smoothing the scatter-corrected data D1 in the channel direction.

As a result of applying different scatter correction factors R(d, do) to adjacent channels, the difference in scatter-corrected data D1 between the adjacent channels is magnified beyond the difference in original data D0, possibly resulting in formation of a step-like difference.

According to the scatter correction method of the ninth aspect, the data D1 can be smoothed in the channel direction to obtain data D2 smoothly continuous in the channel direction.

In its tenth aspect, the present invention provides the scatter correction method having the aforementioned configuration, characterized in comprising determining a high frequency component H0 by high-pass processing (high frequency component extraction processing) scatter-uncorrected data D0 in the channel direction or subtracting smoothed and scatter-uncorrected data D0 from the scatter-uncorrected data D0; and obtaining scatter-corrected and high-frequency-corrected data D3 by adding the high frequency component H0 to the scatter-corrected and smoothed data D2.

The scatter-corrected and smoothed data D2 has lost the high frequency component that the original data D0 contained.

According to the scatter correction method of the tenth aspect, a high frequency component H0 is extracted from the original data D0, and is added to the data D2 to obtain data D3. Thus, the high frequency component can be restored.

In its eleventh aspect, the present invention provides the scatter correction method having the aforementioned configuration, characterized in comprising; determining a high frequency component H0 by high-pass processing scatter-uncorrected data D0 in the channel direction or subtracting smoothed and scatter-uncorrected data D0 from the scatter-uncorrected data D0; determining a regulated high frequency component H1 by multiplying the high frequency component H0 by a regulating factor G(d, do); and obtaining scatter-corrected and high-frequency-corrected data D3 by adding the regulated high frequency component H1 to the scatter-corrected and smoothed data D2.

Since the scatter-corrected and smoothed data D2 is smaller than the original data D0, it is preferable to add a high frequency component H0 whose magnitude is regulated accordingly.

According to the scatter correction method of the eleventh aspect, a high frequency component H0 is extracted from the original data D0, multiplied by a regulating factor G(d, do) and added to the data D2 to obtain data D3. Thus, the high frequency component can be restored with an appropriate magnitude.

The regulating factor G(d, do) that is employed may be a constant supplied by a human operator, a product of a constant supplied by the operator and a corresponding scatter correction factor R(d, do), a corresponding scatter correction factor R(d, do) itself, or an average value of the scatter correction factor R(d, do).

In its twelfth aspect, the present invention provides an X-ray CT apparatus characterized in comprising: an X-ray tube; a multi-row detector; scanning means for collecting data while relatively rotating at least one of said X-ray tube and said multi-row detector around a subject; and scatter measuring means for measuring data I(do, do) by imaging an object to be imaged with a beam thickness equal to a detector thickness do, measuring data I(d, do) by imaging the object to be imaged with a beam thickness d larger than the detector thickness do, and determining an amount of scatter S(d, do) based on a difference between said data I(do, do) and said data I(d, do).

According to the X-ray CT apparatus of the twelfth aspect, the scatter measurement method of the first aspect can be suitably implemented.

In its thirteenth aspect, the present invention provides an X-ray CT apparatus characterized in comprising: an X-ray tube; a multi-row detector; scanning means for collecting data while relatively rotating at least one of said X-ray tube and said multi-row detector around a subject; and scatter measuring means for measuring data I(do, do) by imaging an object to be imaged with a beam thickness equal to a detector thickness do, measuring data I(d, do) by imaging the object to be imaged with a beam thickness d larger than the detector thickness do, and determining a scatter correction factor R(d, do) based on a ratio between said data I(do, do) and said data I(d, do).

According to the X-ray CT apparatus of the thirteenth aspect, the scatter measurement method of the second aspect can be suitably implemented.

In its fourteenth aspect, the present invention provides the X-ray CT apparatus having the aforementioned configuration, characterized in comprising: scatter correction factor storing means for storing a projection p of the object to be imaged and the scatter correction factor or smoothed scatter correction factor R(d, do) in association with each other.

According to the X-ray CT apparatus of the fourteenth aspect, the scatter measurement method of the third aspect can be suitably implemented.

In its fifteenth aspect, the present invention provides the X-ray CT apparatus having the aforementioned configuration, characterized in comprising: scatter correction factor storing means for storing a sum Ar of the projection p of the object to be imaged in a detector row direction or a sum Ac thereof in a channel direction, and the scatter correction factor or smoothed scatter correction factor R(d, do) in association with each other.

According to the X-ray CT apparatus of the fifteenth aspect, the scatter measurement method of the fourth aspect can be suitably implemented.

In its sixteenth aspect, the present invention provides the X-ray CT apparatus having the aforementioned configuration, characterized in comprising: scatter correction factor storing means for storing a sum V of the projection p of the object to be imaged in a detector row direction and channel direction, the projection p of the object to be imaged, and the scatter correction factor or smoothed scatter correction factor R(d, do) in association with each other.

According to the X-ray CT apparatus of the sixteenth aspect, the scatter measurement method of the fifth aspect can be suitably implemented.

In its seventeenth aspect, the present invention provides an X-ray CT apparatus characterized in comprising: an X-ray tube; a multi-row detector; scanning means for collecting data while relatively rotating at least one of said X-ray tube and said multi-row detector around a subject; scatter correction factor storing means for storing a projection p of an object to be imaged and a scatter correction factor or smoothed scatter correction factor R(d, do) in association with each other; and scatter correcting means for determining a projection p from data D0 collected by imaging a subject by an X-ray beam with a beam thickness d using a detector with a detector thickness do, reading the scatter correction factor R(d, do) associated with that projection p from said scatter correction factor storing means, and obtaining scatter-corrected data D1 by multiplying the data D0 by the scatter correction factor R(d, do).

According to the X-ray CT apparatus of the seventeenth aspect, the scatter correction method of the sixth aspect can be suitably implemented.

In its eighteenth aspect, the present invention provides an X-ray CT apparatus characterized in comprising: an X-ray tube; a multi-row detector; scanning means for collecting data while relatively rotating at least one of said X-ray tube and said multi-row detector around a subject; scatter correction factor storing means for storing a sum Ar of a projection p of an object to be imaged in a detector row direction or a sum Ac thereof in a channel direction, and a scatter correction factor or smoothed scatter correction factor R(d, do) in association with each other; and scatter correcting means for imaging a subject by an X-ray beam with a beam thickness d to obtain a projection p, determining a sum Ar of the projection p in the detector row direction or sum Ac thereof in the channel direction, reading the scatter correlation factor R(d, do) associated with the sum Ar or Ac from said scatter correction factor storing means, and obtaining scatter-corrected data D1 by multiplying the data D0 collected using the detector with the detector thickness do by the scatter correction factor R(d, do).

According to the X-ray CT apparatus of the eighteenth aspect, the scatter correction method of the seventh aspect can be suitably implemented.

In its nineteenth aspect, the present invention provides an X-ray CT apparatus characterized in comprising: an X-ray tube; a multi-row detector; scanning means for collecting data while relatively rotating at least one of said X-ray tube and said multi-row detector around a subject; scatter correction factor storing means for storing a sum V of a projection p of an object to be imaged in a detector row direction and channel direction and a scatter correction factor or smoothed scatter correction factor R(d, do) in association with each other; and scatter correcting means for imaging a subject by an X-ray beam with a beam thickness d to obtain a projection p, determining a sum V of the projection p in the detector row direction and channel direction, reading the scatter correction factor R(d, do) associated with the sum V from said scatter correction factor storing means, and obtaining scatter-corrected data D1 by multiplying the data D0 collected using the detector with the detector thickness do by the scatter correction factor R(d, do).

According to the X-ray CT apparatus of the nineteenth aspect, the scatter correction method of the eighth aspect can be suitably implemented.

In its twentieth aspect, the present invention provides the X-ray CT apparatus having the aforementioned configuration, characterized in comprising: smoothing means for obtaining scatter-corrected and smoothed data D2 by smoothing the scatter-corrected data D1 in the channel direction.

According to the X-ray CT apparatus of the twentieth aspect, the scatter correction method of the ninth aspect can be suitably implemented.

In its twenty-first aspect, the present invention provides the X-ray CT apparatus having the aforementioned configuration, characterized in comprising: high-pass processing means for determining a high frequency component H0 by high-pass processing scatter-uncorrected data D0 in the channel direction or subtracting smoothed and scatter-uncorrected data D0 from the scatter-uncorrected data D0; and high-frequency correcting means for obtaining scatter-corrected and high-frequency-corrected data D3 by adding the high frequency component H0 to the scatter-corrected and smoothed data D2.

According to the X-ray CT apparatus of the twenty-first aspect, the scatter correction method of the tenth aspect can be suitably implemented.

In its twenty-second aspect, the present invention provides the X-ray CT apparatus having the aforementioned configuration, characterized in comprising: high-pass processing means for determining a high frequency component H0 by high-pass processing scatter-uncorrected data D0 in the channel direction or subtracting smoothed and scatter-uncorrected data D0 from the scatter-uncorrected data D0; high frequency component scatter correcting means for determining a regulated high frequency component H1 by multiplying the high frequency component H0 by a regulating factor G(d, do); and high frequency correcting means for obtaining scatter-corrected and high-frequency-corrected data D3 by adding the regulated high frequency component H1 to the scatter-corrected and smoothed data D2.

According to the X-ray CT apparatus of the twenty-second aspect, the scatter correction method of the eleventh aspect can be suitably implemented.

According to the scatter measurement method and X-ray CT apparatus of the present invention, scatter in multi-slice imaging can be measured.

According to the scatter correction method and X-ray CT apparatus of the present invention, scatter in multi-slice imaging can be corrected.

The scatter measurement method, scatter correction method and X-ray CT apparatus of the present invention can be applied to reduce degradation of image quality of a CT image due to scatter in multi-slice imaging.

Further objects and advantages of the present invention will be apparent from the following description of the preferred embodiments of the invention as illustrated in the accompanying drawings.

BRIEF DESCRIPTION OF THE DRAWINGS

FIGS. 3a and 3b are explanatory diagrams showing a process of scatter measurement.

FIG. 4 is a conceptual diagram showing a stored scatter correction factor.

DETAILED DESCRIPTION OF THE INVENTION

The present invention will now be described in more detail with reference to embodiments shown in the accompanying drawings. It should be noted that the present invention is not limited to the embodiments.

Example 1

Figure 1:
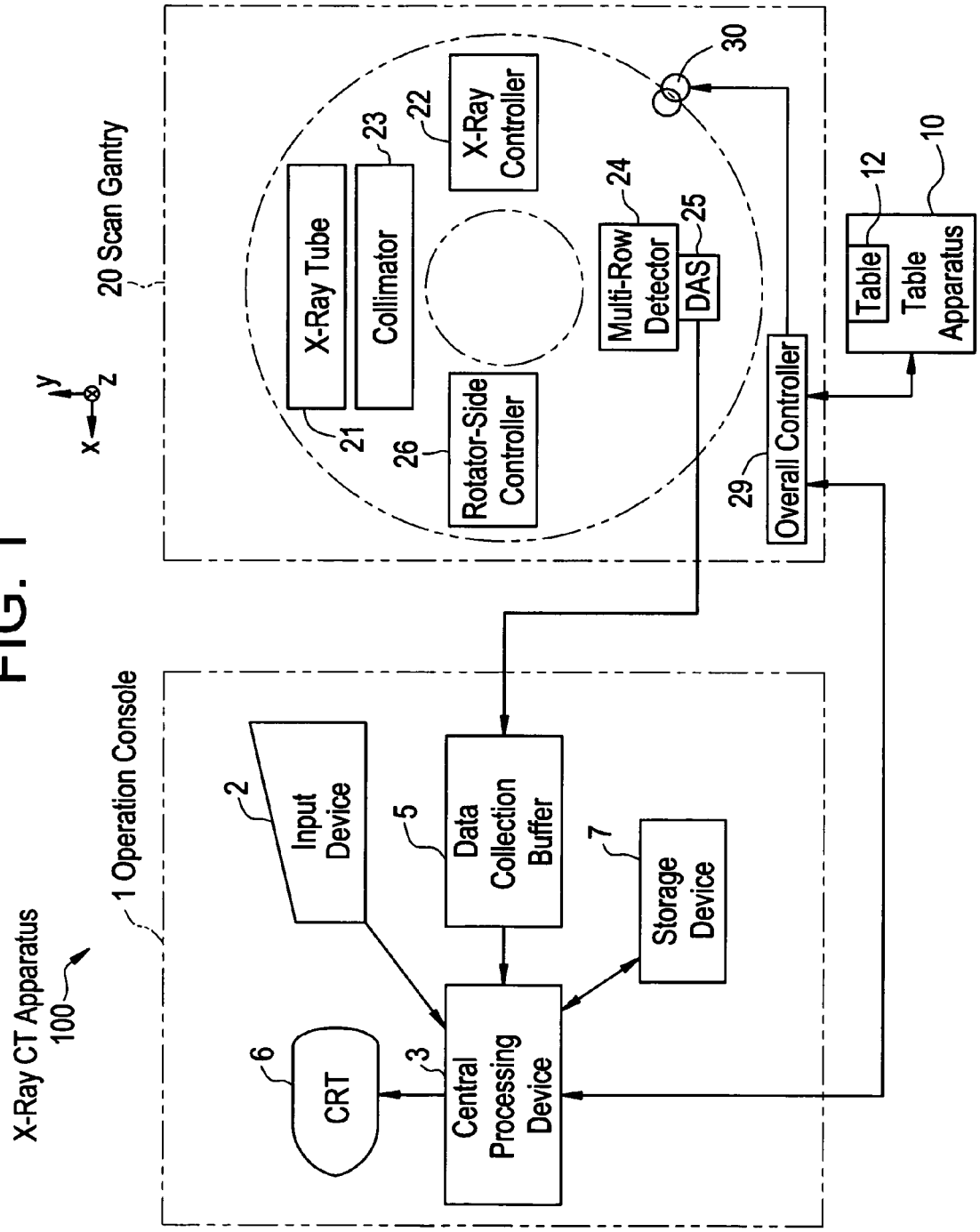
FIG. 1 is a block diagram showing an X-ray CT apparatus in accordance with Example 1.

FIG. 1 is a configuration block diagram showing an X-ray CT apparatus in accordance with Example 1.

The X-ray CT apparatus 100 comprises an operator console 1, a table apparatus 10, and a scan gantry 20.

The operator console 1 comprises an input device 2 for accepting an input by an operator, a central processing apparatus 3 for executing scatter measurement processing, scatter correction processing etc., a data collection buffer 5 for collecting data acquired by the scan gantry 20, a CRT 6 for displaying a CT image reconstructed based on the data, and a storage device 7 for storing programs, data and CT images.

The table apparatus 10 comprises a table 12 for laying thereon a subject and transporting the subject into/out of a bore (cavity) in the scan gantry 20. The table 12 is vertically and horizontally/rectilinearly moved by a motor housed in the table apparatus 10.

The scan gantry 20 comprises an X-ray tube 21, an X-ray controller 22, a collimator 23, a multi-row detector 24, a DAS (data acquisition system) 25, a rotator-side controller 26 for controlling the X-ray controller 22, collimator 23 and DAS 25, an overall controller 29 for communicating control signals and the like with the operator console 1 and table apparatus 10, and a slip ring 30.

Figure 2:
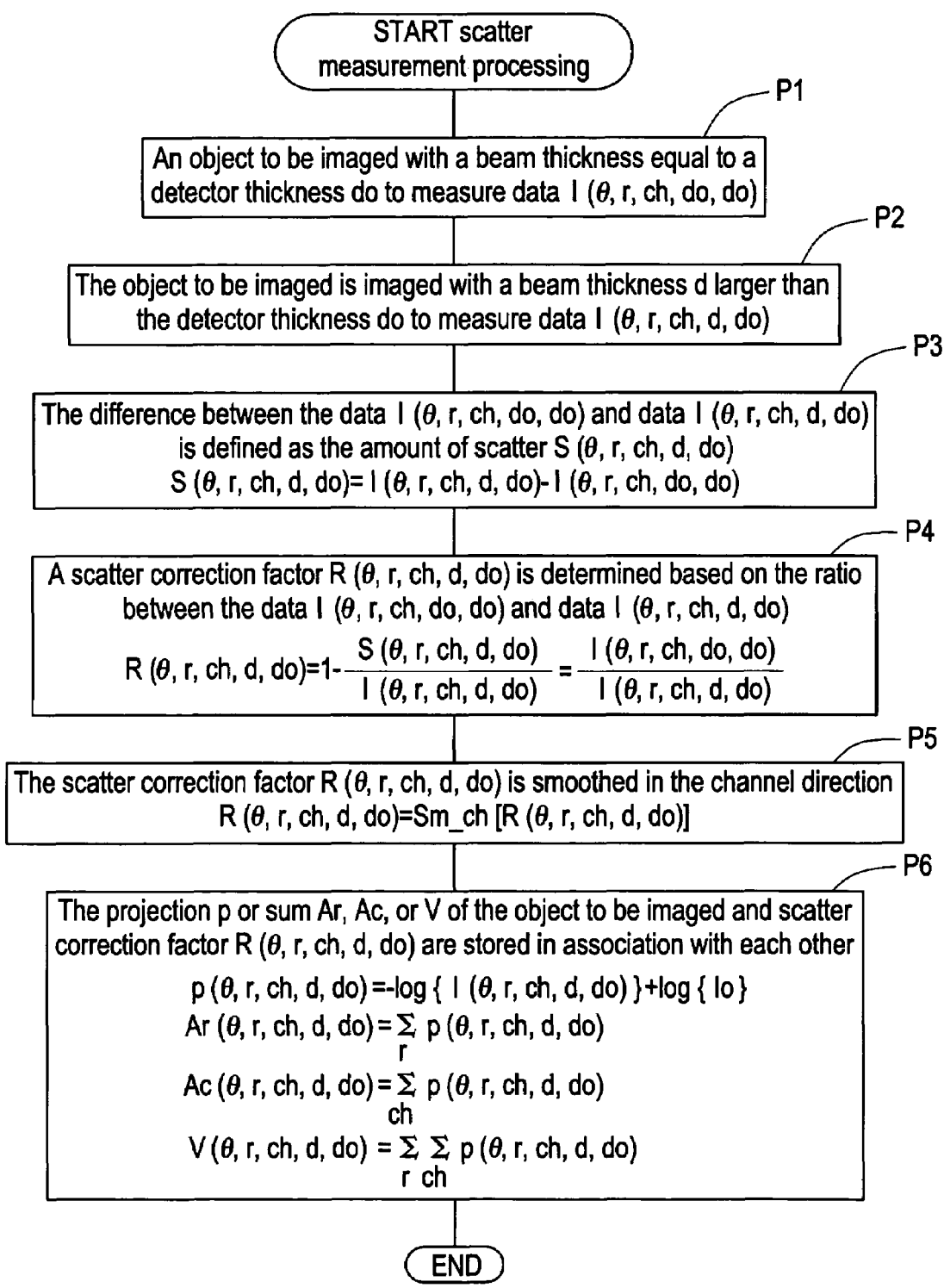
FIG. 2 is a flow chart showing scatter measurement processing in accordance with Example 1.

FIG. 2 is a flow chart showing scatter measurement processing in accordance with Example 1.

At Step P1, as shown in FIG. 3(a), a phantom α is imaged with a beam thickness do equal to a detector thickness do of a detector det(r, ch, do) to measure data I(θ, r, ch, do, do).

The designation (r, ch, do) in the reference to the detector det(r, ch, do) represents (detector row index, channel index, detector thickness).

The designation (θ, r, ch, do, do) in the reference to the data I(θ, r, ch, do, do) represents (fan beam direction, detector row index, channel index, beam thickness, detector thickness).

At Step P2, as shown in FIG. 3(b), the phantom α is imaged with a beam thickness d larger than the detector thickness do of the detector det(r, ch, do) to measure data I(θ, r, ch, d, do).

At Step P3, the difference between the data I(θ, r, ch, do, do) and data I(θ, r, ch, d, do) is defined as an amount of scatter S(θ, r, ch, d, do).

$$S(\theta, r, ch, d, do) = I(\theta, r, ch, d, do) - I(\theta, r, ch, do, do)$$

At Step P4, a scatter correction factor R(θ, r, ch, d, do) is determined based on the ratio between the data I(θ, r, ch, do, do) and data I(θ, r, ch, d, do). That is, $$R(\theta, r, ch, d, do)=1-S(\theta, r, ch, d, do)/I(\theta, r, ch, d, do)$$

or $$R(\theta, r, ch, d, do)=I(\theta, r, ch, do, do)/I(\theta, r, ch, d, do).$$

At Step P5, the scatter correction factor R(θ, r, ch, d, do) is smoothed in the channel direction as follows:

$$R(\theta, r, ch, d, do)=Sm\_ch[R(\theta, r, ch, d, do)],$$

where Sm_ch[R] is a function that smooths in the channel direction the value R distributing from channel to channel.

At Step P6, a projection p of the phantom α is determined as follows:

$$p(\theta, r, ch, d, do)=-\log \{I(\theta, r, ch, d, do)\}+\log \{Io(r, ch)\}.$$

Alternatively, a sum Ar is determined by adding the projection p of the phantom α at the same channel across all detector rows or across a plurality of detector rows including a detector row r as follows:

$$Ar(\theta, r, ch, d, do) = \sum_r p(\theta, r, ch, d, do).$$

Alternatively, a sum Ac is determined by adding the projection p of the phantom α in the same detector row across all channels or across a plurality of channels including a channel ch as follows:

$$Ac(\theta, r, ch, d, do) = \sum_{ch} p(\theta, r, ch, d, do)$$

Alternatively, a sum V is determined by adding the projection p of the phantom α across all detector rows and all channels or across a plurality of detector rows and a plurality of channels including a detector det(r, ch) as follows:

$$V(\theta, r, ch, d, do) = \sum_r \sum_{ch} p(\theta, r, ch, d, do)$$

The projection p or sum Ar, Ac or V of the phantom α and scatter correction factor R(θ, r, ch, d, do) are then stored in association with each other.

The stored scatter correction factor R(θ, r, ch, d, do) is conceptually illustrated in FIG. 4.

There is stored a scatter correction factor R(θ, r, ch, d, do) in association with the fan beam direction θ, detector row index r, channel index ch, beam thickness d, detector thickness do, and projection p or sum Ar, Ac or V of the phantom α.

A scatter correction factor R(r, ch, d, do) may be stored instead on assumption that the scatter correction factor R(θ, r, ch, d, do) remains the same in any fan beam direction θ.

Figure 5:
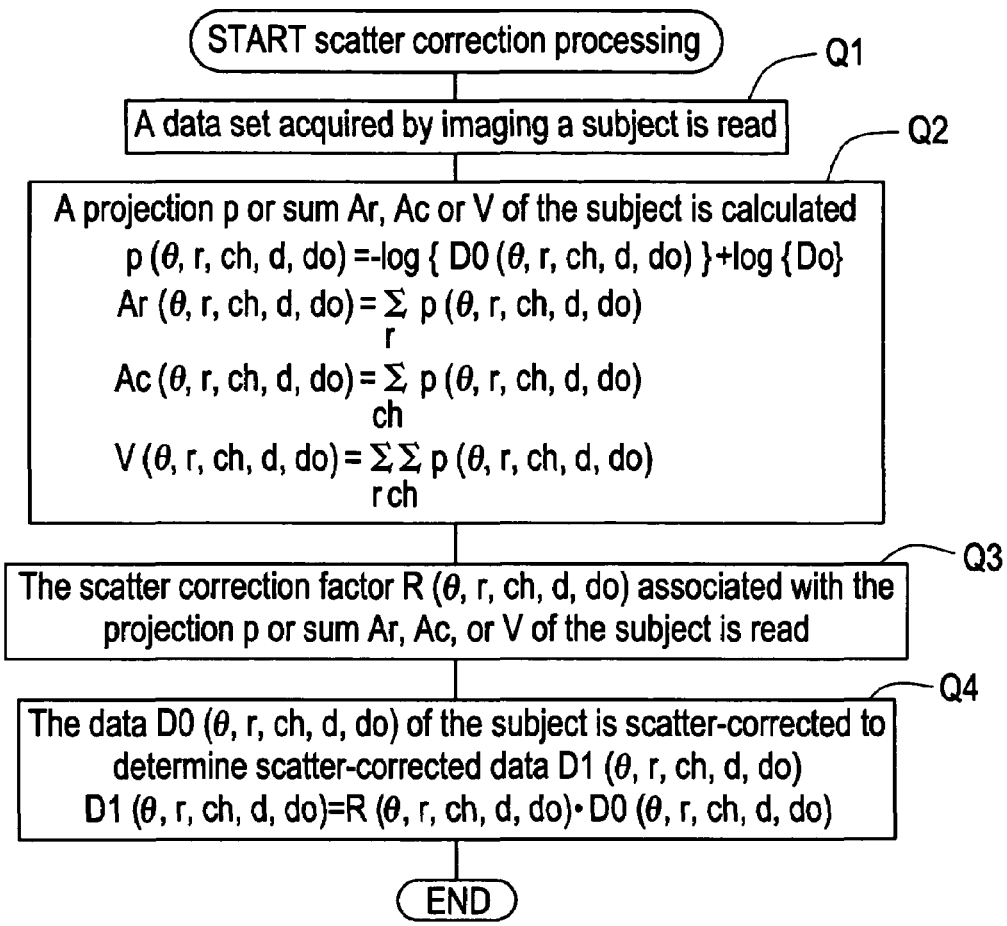
FIG. 5 is a flow chart showing scatter correction processing in accordance with Example 1.

FIG. 5 is a flow chart showing scatter correction processing in accordance with Example 1.

At Step Q1, a data set acquired by imaging a subject is read.

Figure 6:
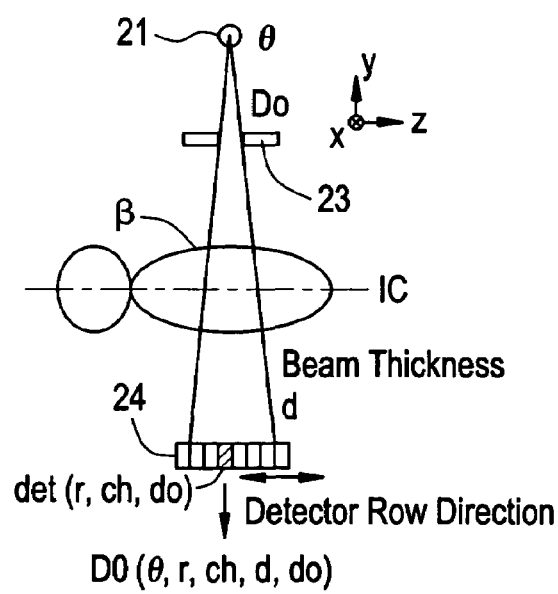
FIG. 6 is an explanatory diagram showing a process of multi-slice imaging.

The data set is a collection of data D0(θ, r, ch, d, do) obtained by imaging a subject β with a beam thickness d larger than the detector thickness do, as shown in FIG. 6, in a range of the fan beam direction θ, detector row r, and channel ch needed in image reconstruction.

At Step Q2, a projection p of the subject is calculated from the data set as follows:

$$p(\theta, r, ch, d, do)=-\log \{D0(\theta, r, ch, d, do)\}+\log \{Do(r, ch)\}.$$

Alternatively, a sum Ar is calculated by adding the projection p of the subject β at the same channel across all detector rows or across a plurality of detector rows including a detector row r as follows:

$$Ar(\theta, r, ch, d, do) = \sum_r p(\theta, r, ch, d, do)$$

Alternatively, a sum Ac is calculated by adding the projection p of the subject β in the same detector row across all channels or across a plurality of channels including a channel ch as follows:

$$Ac(\theta, r, ch, d, do) = \sum_{ch} p(\theta, r, ch, d, do)$$

Alternatively, a sum V is calculated by adding the projection p of the subject β across all detector rows and all channels or across a plurality of detector rows and a plurality of channels including a detector det(r, ch) as follows:

$$V(\theta, r, ch, d, do) = \sum_r \sum_{ch} p(\theta, r, ch, d, do)$$

At Step Q3, the scatter correction factor R(θ, r, ch, d, do) associated with the fan beam direction θ, detector row index r, channel index ch, beam thickness d, detector thickness do, and projection p or sum Ar, Ac or V of the subject β is read.

At Step Q4, the data D0(θ, r, ch, d, do) of the subject β is multiplied by the associated scatter correction factor R(θ, r, ch, d, do) to determine scatter-corrected data D1(θ, r, ch, d, do). The scatter correction processing is then terminated.

Thereafter, a CT image is produced from the scatter-corrected data set of each detector row. Alternatively, a CT image is produced after applying conventionally known scatter correction for a single-row detector to the scatter-corrected data set of each detector row.

According to the X-ray CT apparatus 100 of Example 1, scatter in multi-slice imaging is suitably measured and corrected. Thus, a multi-slice image can be obtained with artifacts due to scatter in multi-slice imaging suppressed.

Example 2

Figure 7:
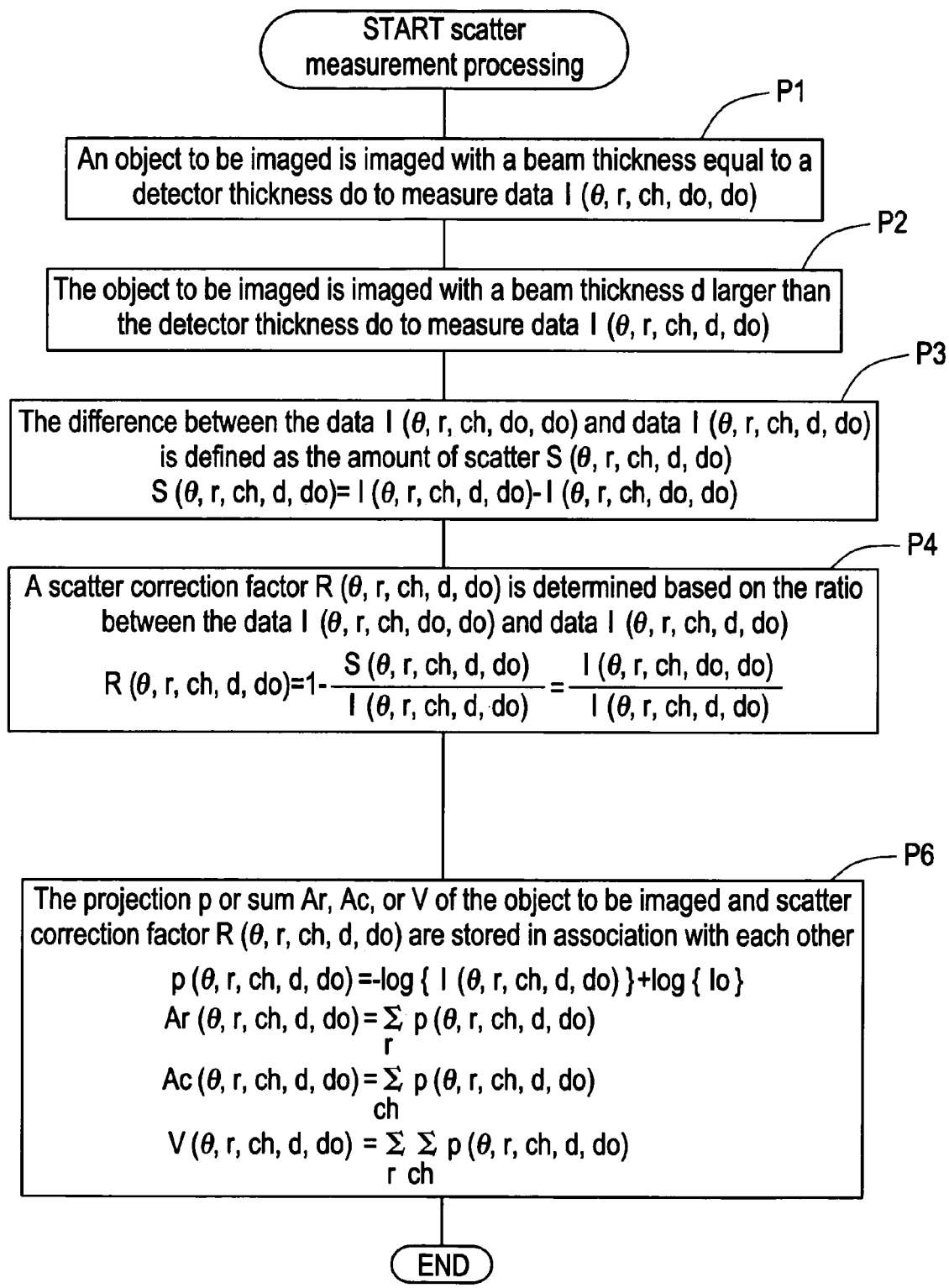
FIG. 7 is a flow chart showing scatter measurement processing in accordance with Example 2.

FIG. 7 is a flow chart showing scatter measurement processing in accordance with Example 2.

The scatter measurement processing is similar to the scatter measurement processing of Example 1 except that Step P5 is omitted.

Specifically, the projection p or sum Ar, Ac or V of the phantom α and an unsmoothed scatter correction factor R(θ, r, ch, d, do) are stored in association with each other.

Figure 8:
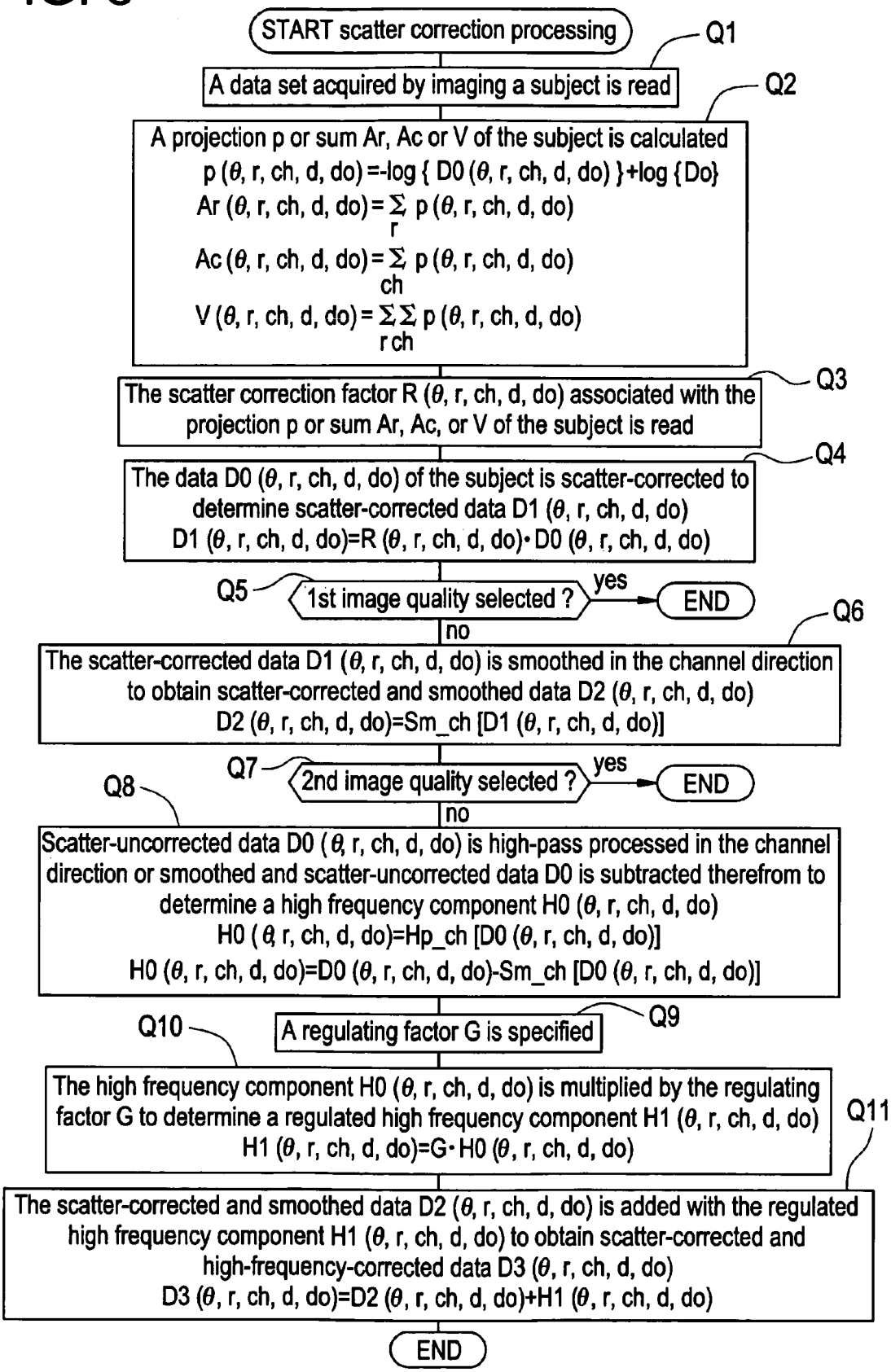
FIG. 8 is a flow chart showing scatter correction processing in accordance with Example 2.

FIG. 8 is a flow chart showing scatter correction processing in accordance with Example 2.

Steps Q1-Q4 are the same as those in Example 1.

However, scatter correction is conducted using the unsmoothed scatter correction factor R(θ, r, ch, d, do) to obtain scatter-corrected data D1(θ, r, ch, d, do).

At Step Q5, the processing is terminated if a first image quality is selected; otherwise, goes to Step Q6.

At Step Q6, the scatter-corrected data D1(θ, r, ch, d, do) is smoothed in the channel direction in each detector row to obtain scatter-corrected and smoothed data D2(θ, r, ch, d, do) as follows:

$$D2(\theta, r, ch, d, do)=Sm\_ch[D1(\theta, r, ch, d, do)].$$

At Step Q7, the processing is terminated if a second image quality is selected; otherwise, goes to Step Q8.

At Step Q8, scatter-uncorrected data D0(θ, r, ch, d, do) is high-pass processed in the channel direction or smoothed and scatter-uncorrected data D0 is subtracted therefrom to determine a high frequency component H0(θ, r, ch, d, do) as follows:

$$H0(\theta, r, ch, d, do)=Hp\_ch\,[D0(\theta, r, ch, d, do)]$$

or $$H0(\theta, r, ch, d, do)=D0(\theta, r, ch, d, do)-Sm\_ch[D0(\theta, r, ch, d, do)],$$

where Hp_ch[D0] is a function that high-pass processes in the channel direction the value D0 distributing from channel to channel.

At Step Q9, a regulating factor G is specified by any one of the following methods:

(1) defining a constant (e.g., 0<constant≦2) supplied by the operator as the regulating factor G;

(2) defining a product of a constant (e.g., 0<constant≦2) supplied by the operator and the scatter correction factor R(θ, r, ch, d, do) associated with data H0(θ, r, ch, d, do) as the regulating factor G(θ, r, ch, d, do) for the data: if the constant is one, the scatter correction factor R(θ, r, ch, d, do) is directly defined as the regulating factor G(θ, r, ch, d, do); and (3) defining an average value of the scatter correction factor R(θ, r, ch, d, do) in the same detector row across all channels or an average value of the scatter correction factor R(θ, r, ch, d, do) across a plurality of channels including a channel ch corresponding to data H0(θ, r, ch, d, do) as the regulating factor G(θ, r, ch, d, do).

At Step Q10, the high frequency component H0(θ, r, ch, d, do) is multiplied by the regulating factor G to determine a regulated high frequency component H1(θ, r, ch, d, do) as follows:

$$H1(\theta, r, ch, d, do)=G \cdot H0(\theta, r, ch, d, do).$$

At Step Q11, the scatter-corrected and smoothed data D2(θ, r, ch, d, do) is added with the regulated high frequency component H1(θ, r, ch, d, do) to obtain scatter-corrected and high-frequency-corrected data D3(θ, r, ch, d, do) as follows. The scatter correction processing is then terminated.

$$D3(\theta, r, ch, d, do)=D2(\theta, r, ch, d, do)+H1(\theta, r, ch, d, do)$$

Thereafter, a CT image is produced from the scatter-corrected data set of each detector row. Alternatively, a CT image is produced after applying conventionally known scatter correction for a single-row detector to the scatter-corrected data set of each detector row.

According to the X-ray CT apparatus of Example 2, scatter in multi-slice imaging is suitably measured and corrected. Thus, a multi-slice image can be obtained with artifacts due to scatter in multi-slice imaging suppressed.

Many widely different embodiments of the invention may be configured without departing from the spirit and the scope of the present invention. It should be understood that the present invention is not limited to the specific embodiments described in the specification, except as defined in the appended claims.

What is claimed is:

1. A scatter measurement method comprising the steps of: measuring data I(do, do) by exposing a beam to a subject with a beam thickness equal to a detector thickness do; measuring data I(d, do) by exposing the beam to the subject with a beam thickness d larger than the detector thickness do; determining a scatter correction factor R(d, do) based on a ratio between said data I(do, do) and said data I(d, do); and reconstructing an image with the determined scatter correction factor R(d, do).

2. The scatter measurement method according to claim 1, further comprising the step of: storing a projection p of the subject and the scatter correction factor or smoothed scatter correction factor R(d, do) in association with each other.

3. The scatter measurement method according to claim 1, further comprising the steps of: collecting data using a multi-row detector; and storing a sum Ar of the projection p of the subject in a detector row direction or a sum Ac thereof in a channel direction, and the scatter correction factor or smoothed scatter correction factor R(d, do) in association with each other.

4. The scatter measurement method according to claim 1, further comprising the steps of: collecting data using a multi-row detector; and storing a sum V of the projection p of the subject in a detector row direction and channel direction, and the scatter correction factor or smoothed scatter correction factor R(d, do) in association with each other.

5. A scatter correction method comprising the steps of: storing a projection p and scatter correction factor or smoothed scatter correction factor R(d, do) in association with each other, wherein projection p is determined from data D0 collected by exposing a subject to an X-ray beam with a beam thickness d using a detector with a detector thickness do, and the scatter correction factor R(d, do) is determined based on an association with projection p; obtaining scatter-corrected data D1 by multiplying the data D0 by the scatter correction factor R(d, do); and reconstructing an image with the scatter-corrected data D1.

6. The scatter correction method according to claim 5, further comprising the step of: obtaining scatter-corrected and smoothed data D2 by smoothing the scatter-corrected data D1 in the channel direction.

7. The scatter correction method according to claim 6, further comprising the steps of: determining a high frequency component H0 by high-pass processing scatter-uncorrected data D0 in the channel direction or subtracting smoothed and scatter-uncorrected data D0 from the scatter-uncorrected data D0; and obtaining scatter-corrected and high-frequency-corrected data D3 by adding the high frequency component H0 to the scatter-corrected and smoothed data D2.

8. A scatter correction method comprising the steps of: storing a sum Ar or Ac of a projection p and scatter correction factor or smoothed scatter correction factor R(d, do) in association with each other, wherein projection p is determined from data collected by exposing a subject to an X-ray beam with a beam thickness d using a multi-row detector including a detector with a detector thickness do, and the sum Ar of the projection p is determined in the detector row direction or the sum Ac thereof is determined in the channel direction; determining the scatter correction factor R(d, do) associated with the sum Ar or Ac; obtaining scatter-corrected data D1 by multiplying the data D0 collected using the detector with the detector thickness do by the scatter correction factor R(d, do); and reconstructing an image with the scatter-corrected data D1.

9. A scatter correction method comprising the steps of: storing a sum V and scatter correction factor or smoothed scatter correction factor R(d, do) in association with each other, wherein projection p is determined from data collected by exposing a subject to an X-ray beam with a beam thickness d using a multi-row detector including a detector with a detector thickness do, and the sum V of the projection p is determined in the detector row direction and channel direction; determining the scatter correction factor R(d, do) associated with the sum V; obtaining scatter-corrected data D1 by multiplying the data D0 collected using the detector with the detector thickness do by the scatter correction factor R(d, do); and reconstructing an image with the scatter-corrected data D1.

10. An X-ray CT apparatus comprising: an X-ray tube; a multi-row detector; a scanning device for collecting data while relatively rotating at least one of said X-ray tube and said multi-row detector around a subject; and a scatter measuring device for measuring data I(do, do) by exposing a beam to a subject with a beam thickness equal to a detector thickness do, measuring data I(d, do) by exposing the beam to the subject with a beam thickness d larger than the detector thickness do, and determining an amount of scatter S(d, do) based on a difference between said data I(do, do) and said data I(d, do).

11. An X-ray CT apparatus comprising: an X-ray tube; a multi-row detector; a scanning device for collecting data while relatively rotating at least one of said X-ray tube and said multi-row detector around a subject; and a scatter measuring device for measurement data I(do, do) by exposing a beam to a subject with a beam thickness equal to a detector thickness do, measuring data I(d, do) by exposing the beam to the subject with a beam thickness d larger than the detector thickness do, and determining a scatter correction factor R(d, do) based on a ratio between said data I(do, do) and said data I(d, do).

12. The X-ray CT apparatus according to claim 11, further comprising: a scatter correction factor storing device for storing a projection p of the subject and the scatter correction factor or smoothed scatter correction factor R(d, do) in association with each other.

13. The X-ray CT apparatus according to claim 11, further comprising: a scatter correction factor storing device for storing a sum Ar of the projection p of the subject in a detector row direction or a sum Ac thereof in a channel direction, and the scatter correction factor or smoothed scatter correction factor R(d, do) in association with each other.

14. The X-ray CT apparatus according to claim 11, further comprising: a scatter correction factor storing device for storing a sum V of the projection p of the subject in a detector row direction and channel direction, the projection p of the object to be imaged, and the scatter correction factor or smoothed scatter correction factor R(d, do) in association with each other.

15. An X-ray CT apparatus comprising: an X-ray tube; a multi-row detector; a scanning device for collecting data while relatively rotating at least one of said X-ray tube and said multi-row detector around a subject; a scatter correction factor storing device for storing a projection p of an object to be imaged and a scatter correction factor or smoothed scatter correction factor R(d, do) in association with each other; and a scatter correcting device for determining a projection p from data D0 collected by imaging a subject by an X-ray beam with a beam thickness d using a detector with a detector thickness do, reading the scatter correction factor R(d, do) associated with that projection p from said scatter correction factor storing device, and obtaining scatter-corrected data D1 by multiplying the data D0 by the scatter correction factor R(d, do).

16. The X-ray CT apparatus according to claim 15, further comprising: a smoothing device for obtaining scatter-corrected and smoothed data D2 by smoothing the scatter-corrected data D1 in the channel direction.

17. The X-ray CT apparatus according to claim 16 further comprising: a high-pass processing device for determining a high frequency component H0 by high-pass processing scatter-uncorrected data D0 in the channel direction or subtracting smoothed and scatter-uncorrected data D0 from the scatter-uncorrected data D0; and a high-frequency correcting device for obtaining scatter-corrected and high-frequency-corrected data D3 by adding the high frequency component H0 to the scatter-corrected and smoothed data D2.

18. The X-ray CT apparatus according to claim 16 further comprising: a high-pass processing device for determining a high frequency component H0 by high-pass processing scatter-uncorrected data D0 in the channel direction or subtracting smoothed and scatter-uncorrected data D0 from the scatter-uncorrected data D0; a high frequency component scatter correcting device for determining a regulated high frequency component H1 by multiplying the high frequency component H0 by a regulating factor G(d, do); and a high frequency correcting device for obtaining scatter-corrected and high-frequency-corrected data D3 by adding the regulated high frequency component H1 to the scatter-corrected and smoothed data D2.

19. An X-ray CT apparatus comprising: an X-ray tube; a multi-row detector; a scanning device for collecting data while relatively rotating at least one of said X-ray tube and said multi-row detector around a subject; a scatter correction factor storing device for storing a sum Ar of a projection p of an object to be imaged in a detector row direction or a sum Ac thereof in a channel direction, and a scatter correction factor or smoothed scatter correction factor R(d, do) in association with each other; and a scatter correcting device for imaging a subject by an X-ray beam with a beam thickness d to obtain a projection p, determining a sum Ar of the projection p in the detector row direction or sum Ac thereof in the channel direction, reading the scatter correction factor R(d, do) associated with the sum Ar or Ac from said scatter correction factor storing device, and obtaining scatter-corrected data D1 by multiplying the data D0 collected using the detector with the detector thickness do by the scatter correction factor R(d,do).

20. An X-ray CT apparatus comprising: an X-ray tube; a multi-row detector; a scanning device for collecting data while relatively rotating at least one of said X-ray tube and said multi-row detector around a subject; a scatter correction factor storing device for storing a sum V of a projection p of an object to be imaged in a detector row direction and channel direction and a scatter correction factor or smoothed scatter correction factor R(d, do) in association with each other; and a scatter correcting device for imaging a subject by an X-ray beam with a beam thickness d to obtain a projection p, determining a sum V of the projection p in the detector row direction and channel direction, reading the scatter correction factor R(d, do) associated with the sum V from said scatter correction factor storing device, and obtaining scatter-corrected data D1 by multiplying the data D0 collected using the detector with the detector thickness do by the scatter correction factor R(d, do).

* * * * *